(12) United States Patent
Sczaniecka et al.

(10) Patent No.: US 10,722,212 B2
(45) Date of Patent: Jul. 28, 2020

(54) GUIDE SHEATH WITH WINDOW AND MARKINGS INDICATING LOCATION THEREOF

(71) Applicant: Spiration, Inc., Redmond, WA (US)

(72) Inventors: Anna K. Sczaniecka, Redmond, WA (US); Hugo X. Gonzalez, Woodinville, WA (US); David H. Dillard, Grapeview, WA (US)

(73) Assignee: Gyrus ACMI, Inc., Southborough, MA (US)

( * ) Notice: Subject to any disclaimer, the term of this patent is extended or adjusted under 35 U.S.C. 154(b) by 771 days.

(21) Appl. No.: 15/475,339

(22) Filed: Mar. 31, 2017

(65) Prior Publication Data

US 2018/0279868 A1    Oct. 4, 2018

(51) Int. Cl.
| | |
|---|---|
| *A61B 8/12* | (2006.01) |
| *A61B 8/00* | (2006.01) |
| *A61B 1/00* | (2006.01) |
| *A61B 1/018* | (2006.01) |

(52) U.S. Cl.
CPC .............. *A61B 8/12* (2013.01); *A61B 1/0005* (2013.01); *A61B 1/018* (2013.01); *A61B 8/4245* (2013.01); *A61B 8/445* (2013.01); *A61B 8/4483* (2013.01); *A61B 8/461* (2013.01)

(58) Field of Classification Search
CPC ......... A61B 1/0005; A61B 1/018; A61B 8/12; A61B 8/445; A61B 8/4483; A61B 8/461; A61B 8/4245
See application file for complete search history.

(56) References Cited

U.S. PATENT DOCUMENTS

| | | | |
|---|---|---|---|
| 4,951,677 A | 8/1990 | Crowley et al. | |
| 6,283,951 B1 * | 9/2001 | Flaherty | A61B 17/11 604/164.11 |
| 2014/0277036 A1 * | 9/2014 | Flynn | A61B 17/3205 606/170 |

* cited by examiner

*Primary Examiner* — Amelie R Davis (57) ABSTRACT

A system for determining orientation of a guide sheath introduced by a bronchoscope or similar device. An example system includes a display device, a scope device and a guide sheath. The guide sheath includes a window occupying a predefined circumferential sector of a distal end of the guide sheath and a plurality of markings configured to visually indicate location/orientation and/or distance of the window. The plurality of markings includes a plurality of first markings located along a longitudinal center axis of the window and a plurality of second markings located along one or more other longitudinal axes that are radially separated from the longitudinal center axis of the window by more than 45°.

19 Claims, 9 Drawing Sheets

GUIDE SHEATH WITH WINDOW AND MARKINGS INDICATING LOCATION THEREOF

BACKGROUND

The statements in this section merely provide background information related to the present disclosure and may not constitute prior art.

The tools that are currently available for the ultrasound visualization and sampling of peripheral tumors are limited in their range of motion and diagnostic capabilities. Typically, during peripheral sampling a guide sheath is fed through a bronchoscope and extended so far beyond the reach of the bronchoscope that the distal end of the guide sheath is not visible. A radial endobronchial ultrasound (EBUS) miniprobe is then threaded through the guide sheath and used to determine the approximate location of the tumor.

Unfortunately, a peripheral tumor that is located off to one side of an airway (as opposed to one that is centered around an airway) has a substantially lower diagnostic yield in part due to the limitations of current radial EBUS technology, which allows the operator to discern the depth from the probe, but not the direction of the tumor.

SUMMARY

The present invention provides an improved guide sheath for use with a medical scope, such as a bronchoscope.

Accordingly, pursuant to one aspect of the present invention, an example system includes a display device, a scope device and a guide sheath. A radial ultrasound device, a sampling device or medicant delivery device may be inserted through the guide sheath. The guide sheath includes a window occupying a predefined circumferential sector of a distal end of the guide sheath. The window may be an actual opening in the guide sheath to be used in conjunction with an ultrasound gel or another substance conducive to ultrasound or the window may be a portion of the guide sheath that is ultrasound permeable, distinct from the material of the remainder of the guide sheath. The radial ultrasound device includes a radial transducer that can be positioned at the window and configured to send image signals to the display device. The window may also be a port for allowing passage of a sampling device or a device for delivering a medicant. In addition, the guide sheath includes a plurality of markings configured to visually indicate location of the window. The plurality of markings includes a plurality of first markings located along a longitudinal center axis of the window and a plurality of second markings located along one or more other longitudinal axes that are radially separated from the longitudinal center axis of the window by more than 45°.

In one aspect of the invention, the scope device includes a handle, an insertion tube having a proximal end attached to the handle. The insertion tube includes a working channel and a camera located at a distal end of the insertion tube adjacent to the working channel. The camera generates images approximately along a longitudinal axis associated with the insertion tube.

In another aspect of the invention, the plurality of first markings includes two or more pointer markers that point along the longitudinal center axis towards the window.

In still another aspect of the invention, the plurality of second markings includes two or more pointer markings that point in the shortest direction towards the longitudinal center axis of the window along the circumference of the guide sheath.

In yet another aspect of the invention, the plurality of second markings includes two or more non-pointer markers located on a side of the guide sheath that is approximately opposite to a side associated with the window.

In still yet another aspect of the invention, at least a portion of the plurality of first markers indicates a distance value associated with the window for a center of the window.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, emphasis instead being placed upon illustrating the principles of the invention. In the drawings:

FIG. 3-1 illustrates a partial side view of the distal end of a sheath formed in accordance with an embodiment of the present invention;

FIG. 3-2 illustrates a partial view of a second side of the sheath shown in FIG. 3-1;

FIG. 3-3 illustrates a partial view of a third side of a first side of the sheath of FIG. 3-1;

FIG. 3-4 illustrates a partial view of a fourth side of the sheath of FIG. 3-1;

FIGS. 11-1 and 11-2 illustrate side cross-section views of a guide sheath with internal ramp formed in accordance with an embodiment of the present invention; and FIGS. 12-1, 12-2 and 12-3 are views of an example guide sheath with internal catheter formed in accordance with an embodiment of the present invention.

DETAILED DESCRIPTION

The following description is merely exemplary in nature and is not intended to limit the present disclosure, application, or uses.

Figure 1:
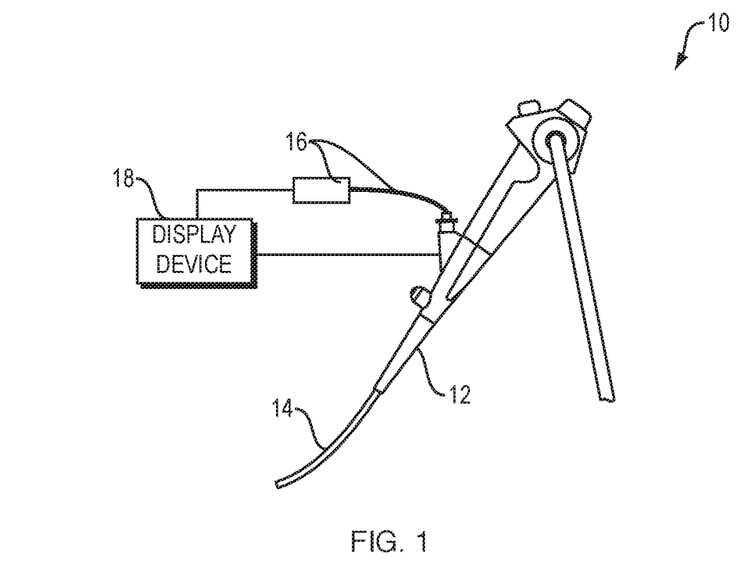
FIG. 1 illustrates an example of a bronchoscope system formed in accordance with the principles of the present invention.

Referring now to FIG. 1, a bronchoscope system 10 includes a bronchoscope 12 with an insertion tube 14, a radial ultrasound device 16 and a display device 18. A sampling device or a medicant delivery device, such as a needle, may be used with the bronchoscope 12. The display device 18 is in wired or wireless signal communication with the bronchoscope 12 and/or the radial ultrasound device 16. The display device 18 presents images generated based on information received from bronchoscope 12 and/or the radial ultrasound device 16. A diagnostic bronchoscope (e.g., BF-X190 produced by Olympus®) is an example of the bronchoscope 12 and the radial endobronchial ultrasound (EBUS) miniprobes produced by Olympus® are examples of the radial ultrasound device 16.

Figure 2:
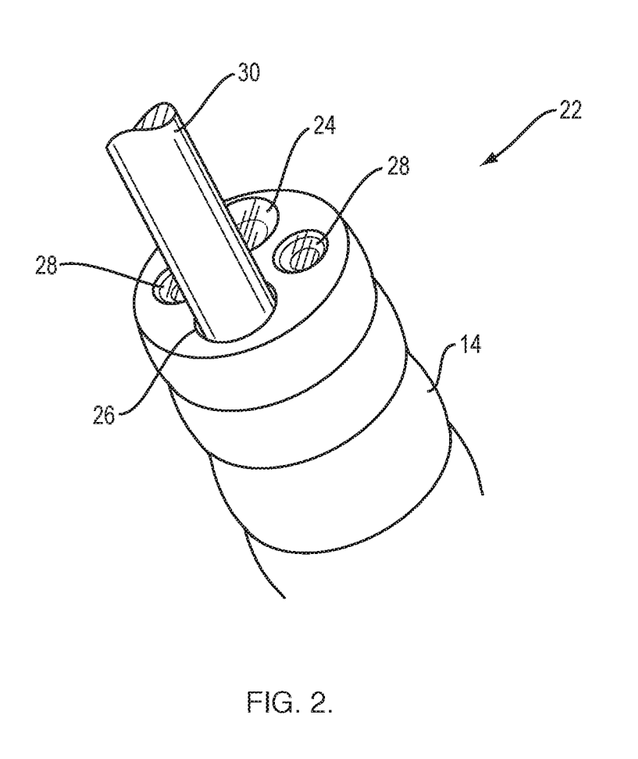
FIG. 2 illustrates a close-up view of the distal end of an insertion tube of the system shown in FIG. 1.

As shown in FIG. 2, a distal end 22 of the insertion tube 14 includes a working channel 26, a camera 24 and one or more lights 28. In certain procedures, a guide sheath 30 is received within the working channel 26 of the bronchoscope 12 through the insertion tube 14 to exit the distal end 22. The camera 24 and light(s) 28 are directed distantly such that they illuminate and capture images still and/or video) of at least the guide sheath 30 and surrounding tissue as the guide sheath 30 extends distally from the insertion tube 14.

Figure 31:
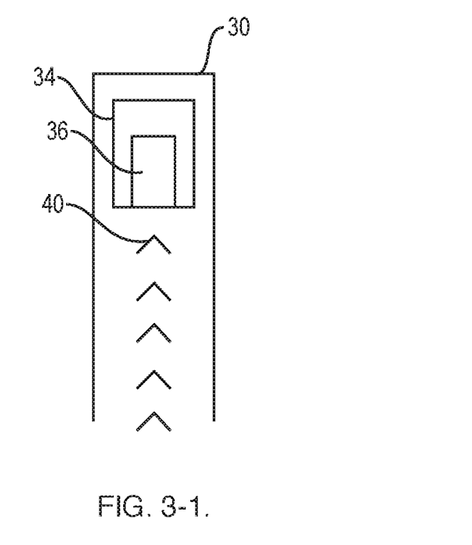

As shown in FIG. 3-1, the distal end 22 of the guide sheath 30 includes a side window 34 through which a needle (not shown) could pass. Also, a transducer 36 of the radial ultrasound device 16 may be exposed to surrounding tissue at the side window 34. The distal end of the guide sheath 30 beyond the side window 34 may be sealed to facilitate lateral movement of a needle and/or keep the transducer 36 of the radial ultrasound device 16 from protruding beyond the end of the guide sheath 30. Instead of protracting the radial ultrasound transducer 36 beyond the distal tip of the guide sheath 30 as it currently done, the transducer 36 remains within the guide sheath 30. This allows the radial ultrasound transducer 36 to selectively receive signals from the side window 34 and not the surrounding guide sheath 30, due to the guide sheath 30 being impermeable to ultrasound signals. This allows the operator to determine the orientation of the target tissue (e.g., lesion) relative to the guide sheath 30 and thus the insertion tube 14 due to markings on the guide sheath 30.

The window 34 may be an actual opening in the guide sheath or the window may be a portion of the guide sheath that is ultrasound permeable, distinct from the material of the remainder of the guide sheath. The window 34 may also be a port for allowing passage of a sampling device or a device for delivering a medicant (e.g., needle).

Typically, during peripheral sampling the guide sheath 30 is extended so far out of the insertion tube 14 that the distal end of the guide sheath 30 is not visible. Markings 40-46 are included along the distal portion of the guide sheath 30. The markings 40-46 are viewable in images produced by the camera 24 and presented on the display device 18, thus making the operator aware of the orientation of the side window 34 relative to the point of view of the camera 24. The markings 40-46 may include arrows or triangles that point the user in the direction of the side window 34, colors to indicate the orientation of the side window 34 or some other indicators. The operator can change the orientation of the side window 34 by turning the proximal portion of the guide sheath 30. While force applied to proximal portion of the guide sheath 30 will most likely not translate perfectly to the distal portion of the guide sheath 30, the markings 40-46 on the guide sheath 30 allow the operator to discern the orientation of the side window 34 relative to the point of view of the camera 24.

Figure 32:
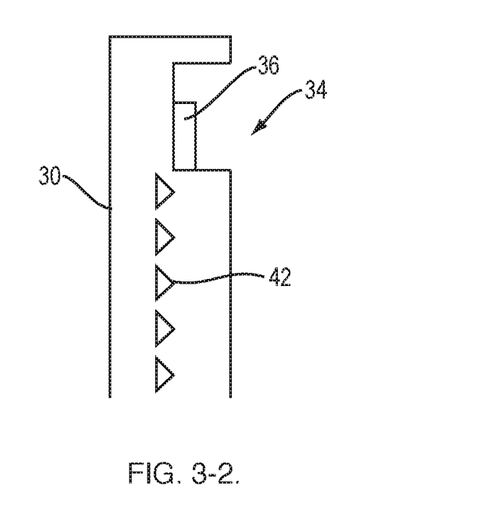
Figure 34:
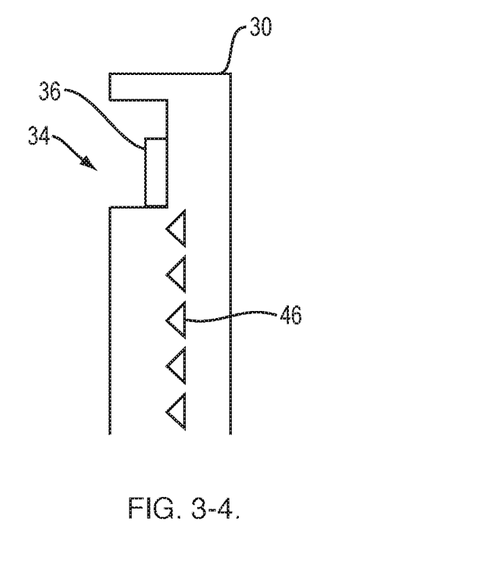
Figure 111:
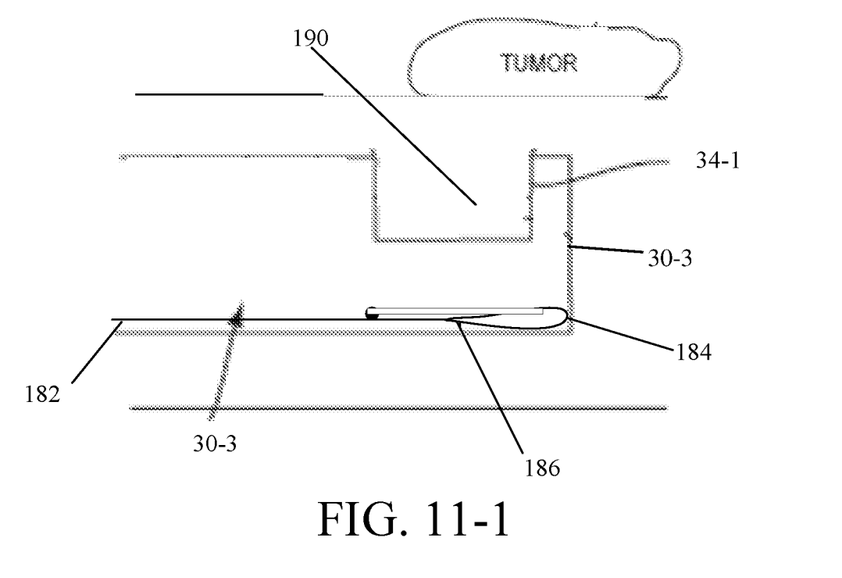
Figure 112:
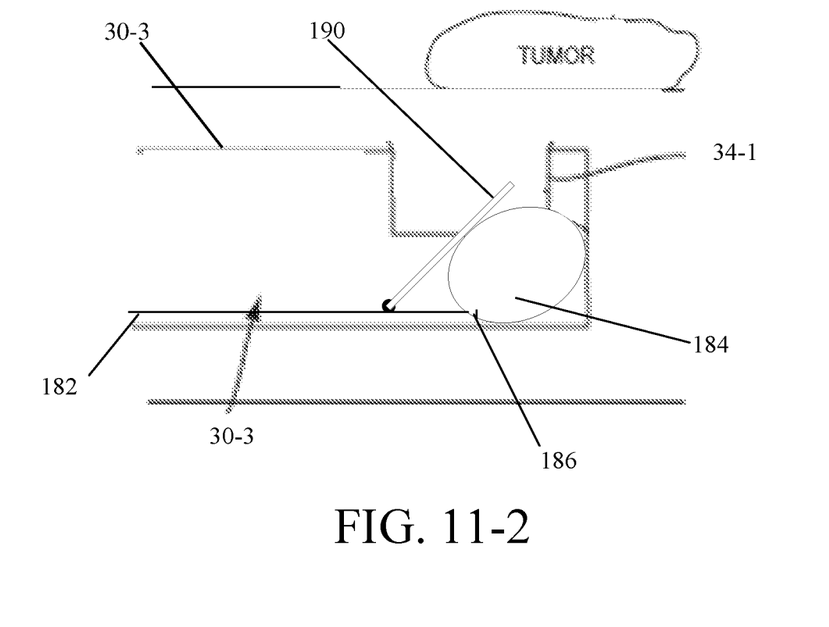
Figure 121:
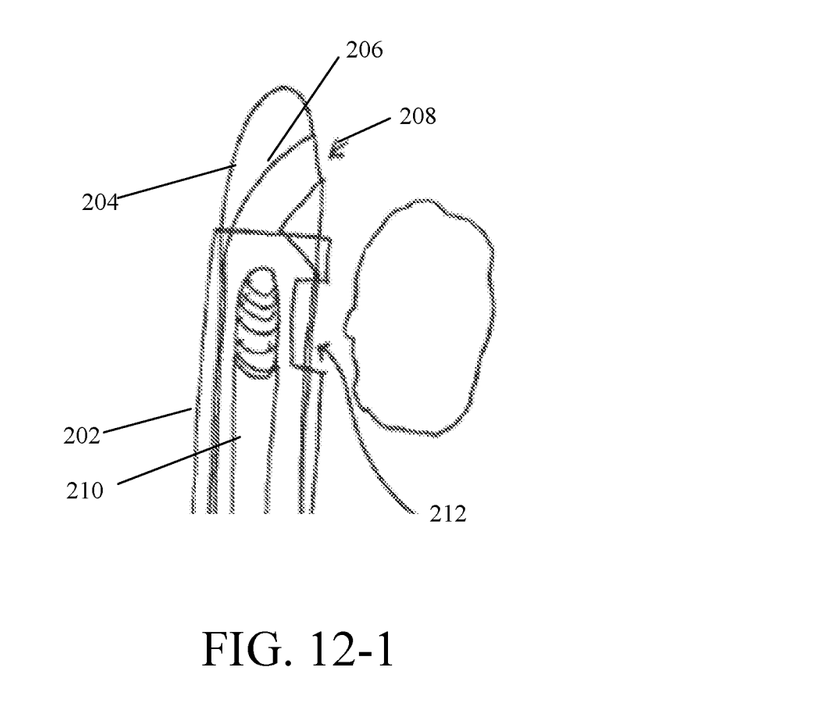

As shown in FIG. 3-1, the markings 40 located on a side of the guide sheath 30 that coincides with the side window 34 include arrows that point to the side window 34. The markings 40 are centered on a longitudinal centerline of the side window 34. As shown in FIGS. 3-2 and 3-4, the markings 42 and 46 are triangles or arrows that point toward the side of the guide sheath 30 that includes the side window 34. If lines were extended from the markers 42 and 46 around the circumference of the guide sheath 30, then these lines would perpendicularly intersect with the longitudinal centerline of the side window 34. Thus, when the operator sees the guide sheath 34 showing markings 42 in the image generated by the camera 24, the operator would know that if target tissue appeared in the image produced by the transducer 36, then that target tissue would be located to the right of the current position of the guide sheath 30 regardless of where the feedback associated with the target tissue appears on the image produced by the transducer 36 at the display device 18.

Figure 33:
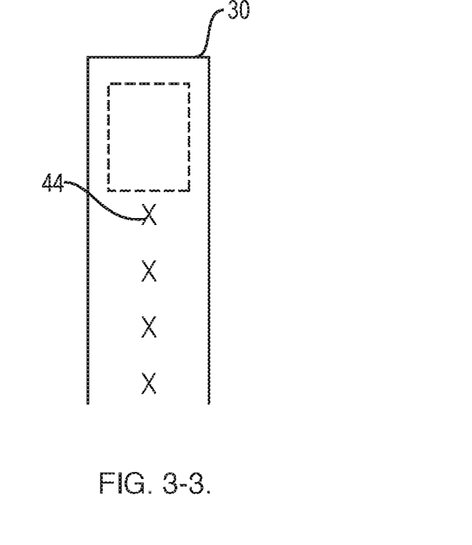

As shown in FIG. 3-3, the markings 44 include "x"s that indicate that the side window 34 is located on the opposite side of the guide sheath 30. Other markings may be included that would similarly indicate that the side window 34 is co-located with the markings, to the immediate left or right of the currently visible side or on the opposite side from the currently visible side.

Figure 4:
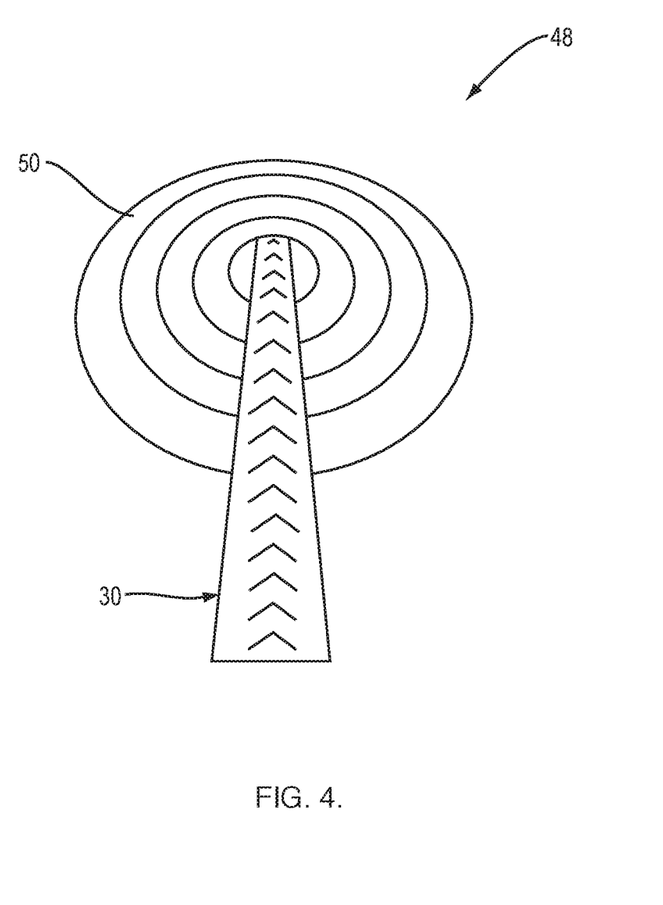
FIG. 4 illustrates an example image produced by a camera of the device of FIGS. 1-1 and 1-2 when inserted into a lumen of a body.

FIG. 4 shows an example image 48 produced by the transducer 24 and presented on the display device 18 of the guide sheath 30 within a lumen 50 of the human body, such as a bronchial tube. As shown, the guide sheath 30 extends from a distal end of the insertion tube 14 into the lumen 50. The image 48 shows the markings 40 pointing towards the side window 34 at the distal end of the guide sheath 30.

Figure 5:
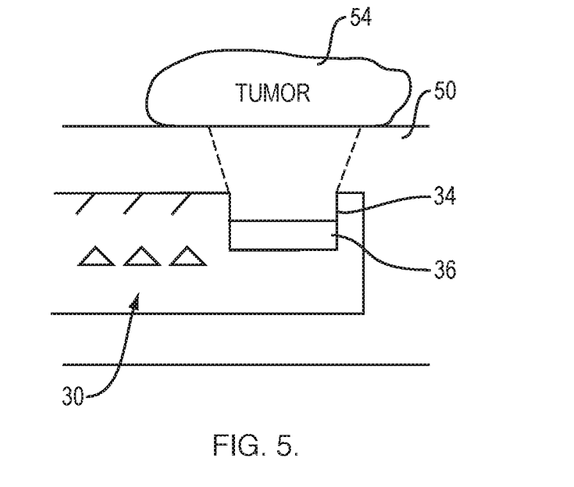
FIG. 5 illustrates a side view of the distal end of a bronchoscope system during ultrasounding of a tumor.
Figure 6:
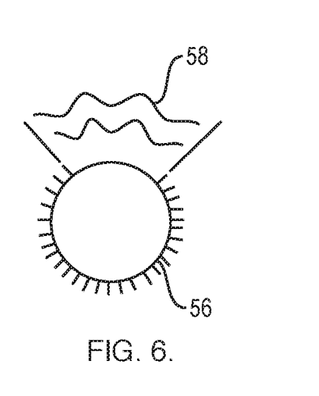
FIG. 6 illustrates an example image produced by the device shown in FIG. 5.

FIG. 5 shows a side view of the very distal end of the guide sheath 30 with the side window 34 directed at a tumor 54 located adjacent to but outside of the lumen 50. The markings 46 point up towards the side of the guide sheath 30 that includes the side window 34. FIG. 6 illustrates an example image generated by the radial ultrasound transducer 36 when used with the guide sheath 30 as shown in FIG. 5. A first feedback area 56 shows noise at a radial distance comparable to the distance between the radial ultrasound transducer 36 and the wall of the guide sheath 30. The first feedback area 56 represents the portion of the guide sheath 30 that is not associated with the side window 34. A second feedback area 58 provides feedback of tissue ultrasonically illuminated through the side window 34. In this example, the second feedback area 58 identifies the tumor 54.

Figure 7:
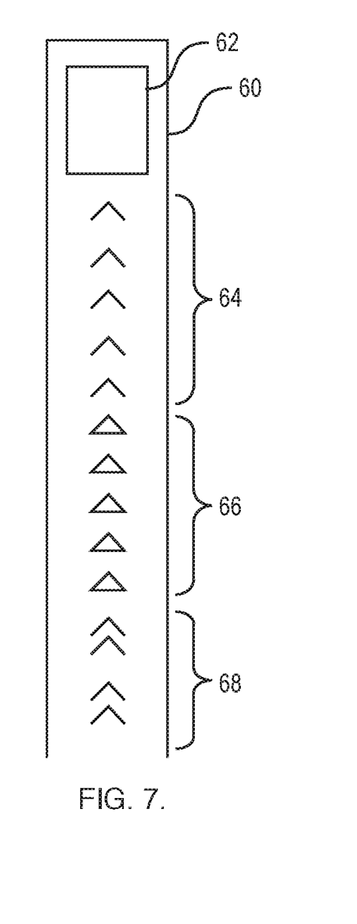
FIG. 7 illustrates a side view of a distal end of an example device formed in accordance with an embodiment of the present invention.

As shown in FIG. 7, a guide sheath 60 includes a side window 62 at the distal end and markings 64-68 along the shaft of the guide sheath 60 along a longitudinal centerline of the side window 62. In this example, the first markings 64 closest to the side window 62 are chevrons, the second markings 66 are triangles and the third markings 68 are double chevrons. The markings 64-68 may include different colors and/or patterns in order to identify a measure of depth from the end of the insertion tube 14 to the side window 34. The markings 64-68 may be at 2 mm increments, at other distance increments or at varying distance increments, Thus, the transition between the first and second markings is approximately 10 mm from the side window 62.

Figure 8:
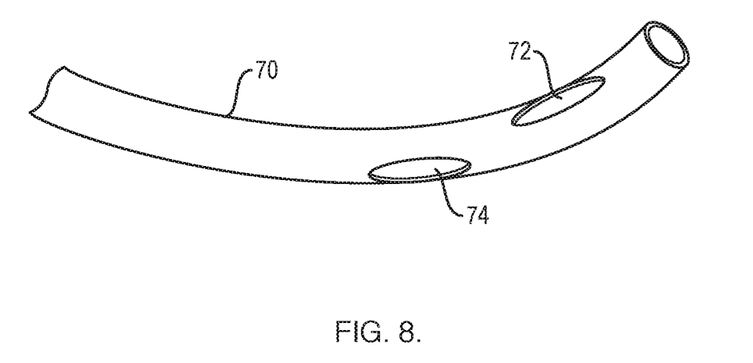
FIG. 8 illustrates a side view of a distal end of an example guide sheath formed in accordance with an embodiment of the present invention.

As shown in FIG. 8, a guide sheath 70 includes first and second side windows 72 and 74. The first and second side windows 72 and 74 are located at different longitudinal positions and different radial positions of the guide sheath 70. The guide sheath 70 may also include one or more sets of markings (not shown) for identifying relative position of one or both of the side windows 72 and 74. The guide sheath 70 may include more than two side windows and more than two sets of markings.

Figure 9:
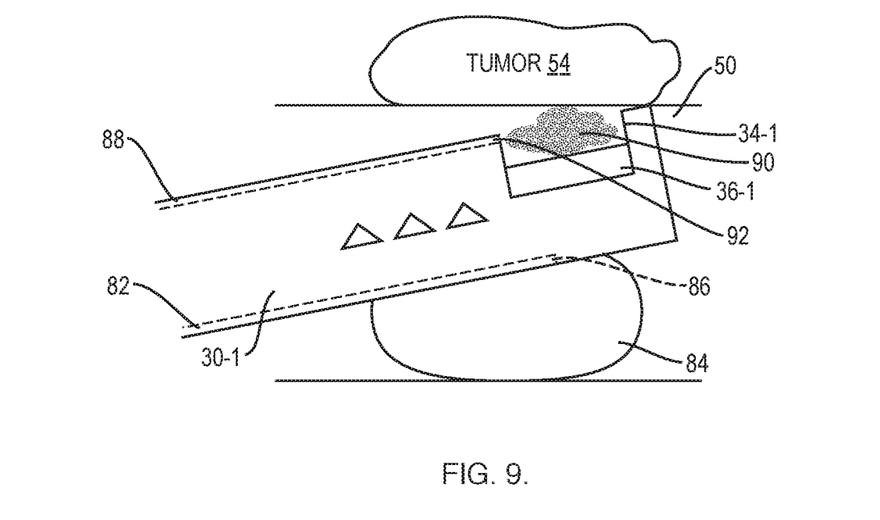
FIG. 9 illustrates a side, partial view of a distal end of an example guide sheath within a human lumen formed in accordance with an embodiment of the present invention.

As shown in FIG. 9, a guide sheath 30-1 includes a main lumen for receiving a transducer 36-1. The main lumen includes a side window 34-1 at a distal end of the guide sheath 30-1. The guide sheath 30-1 includes a second lumen 82 that extends from a proximal handle portion associated with the transducer 36-1. A port 86 at a distal end of the guide sheath 30-1 exposes the second lumen 82 to an environment exterior to the guide sheath 30-1. The port 86 may be significantly smaller than the side window 34-1. In this example, the port 86 is located on an opposite side of the guide sheath 30-1 from the side window 34-1. An inflatable balloon 84, is positioned opposite from the side window 34-1 around the port 86, such that when air or fluid, such as a saline solution, is passed into the second lumen 82, the air or fluid exits the port 86 thus causing the balloon 84 to inflate/expand. The expanded balloon 84 applies a force to the guide sheath 30-1 by pushing against a wall of the passageway. The balloon 84 causes the guide sheath 30-1 to deflect such that a border around the side window 34-1 comes into full or partial abutment with the wall of the lumen 50 of the human body. The port 86 and/or the second lumen 82 may be located other locations around the guide sheath 30-1 provided the port 86 is able to provide air/fluid to the balloon 84.

The guide sheath 30-1 includes a third lumen 88 that extends from the proximal handle portion associated with the transducer 36-1 to the side window 34-1. An ultrasound compatible fluid is sent from the handle portion into the third lumen 88 to exit a port 92 near the side window 34-1. The ultrasound compatible fluid provides a medium for effective ultrasound communication between the transducer 36-1 and targeted tissue (e.g., tumor 54).

The features of FIG. 9 may be used in combination or individually.

Figure 10:
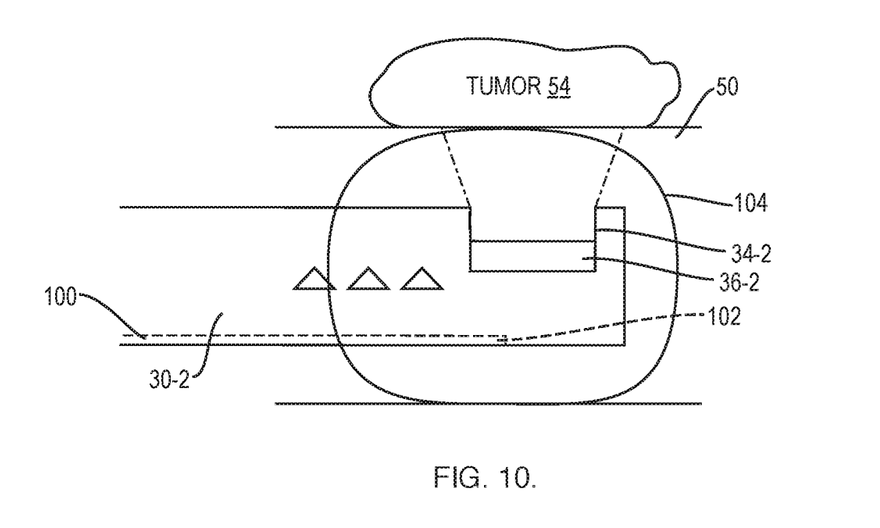
FIG. 10 illustrates a side, partial view of a distal end of an example guide sheath within a human lumen formed in accordance with an embodiment of the present invention.

As shown in FIG. 10, a guide sheath 30-2 includes a main lumen for a transducer 36-2 and a second lumen 100 that extends from a proximal handle portion associated with the transducer 36-2. A port 102 is located at a distal end of the guide sheath 30-2. The port 102 may be significantly smaller than the side window 34-2. An inflatable balloon 104 is positioned around the distal end of the guide sheath 30-2, such that when he fluid, such as a saline solution, is passed into the second lumen 100, the fluid exits the port 102 thus causing the balloon 104 to expand. The fluid in the balloon 104 allows for ultrasound signal communication. The expanded balloon 104 makes contact with the tumor 54 or the wall of the lumen 50, thus allowing for ultrasound signal transmission.

As shown in FIGS. 11-1 and 11-2, a guide sheath 30-3 includes a second lumen 182 that extends from a proximal handle portion. A port 186 at a distal end of the guide sheath 30-3 exposes the second lumen 182 to an environment interior to the guide sheath 30-3. The port 186 may be significantly smaller than the side window 34-1. In this example, the port 186 is located on an opposite side of the guide sheath 30-3 from the side window 34-1. An inflatable balloon 184 is positioned opposite from and distal to the side window 34-1 around the port 186, such that when air or fluid, such as a saline solution, is passed into the second lumen 182, the air or fluid exits the port 186 thus causing the balloon 184 to inflate/expand. The expanded balloon 184 applies a force to a hinged ramp 190 by pushing against the interior walls of the guide sheath 30-3. The balloon 184 causes the hinged ramp 190 to lift such that it angles up towards the side window 34-1 (FIG. 11-2). The hinged ramp 190 then is positioned to deflect any tool passed down the first lumen to be re-directed out of the window 34-1. The guide sheath 30-3 includes markings similar to those on the guide sheath 30 of FIGS. 3-1 thru 3-4.

As shown in FIGS. 12-1, 12-2 and 12-3, a sheath device includes a guide sheath 202 and an internal catheter 204. The internal catheter 204 includes an ultrasound permeable material, an atraumatic tip, and an exit ramp 206. The exit ramp 206 exposes an internal lumen of the internal catheter 204 to the environment outside of the internal catheter 204 via a port 208. The exit ramp 206 directs movement of a needle or other medical tool. The guide sheath 202 includes markings similar to those on the guide sheath 30 of FIGS. 3-1 thru 3-4.

Figure 122:
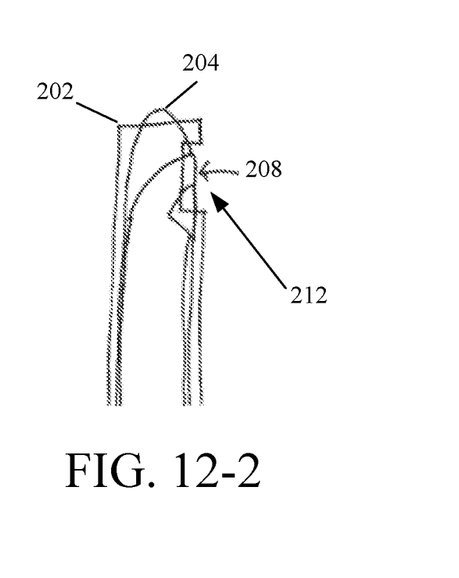
Figure 123:
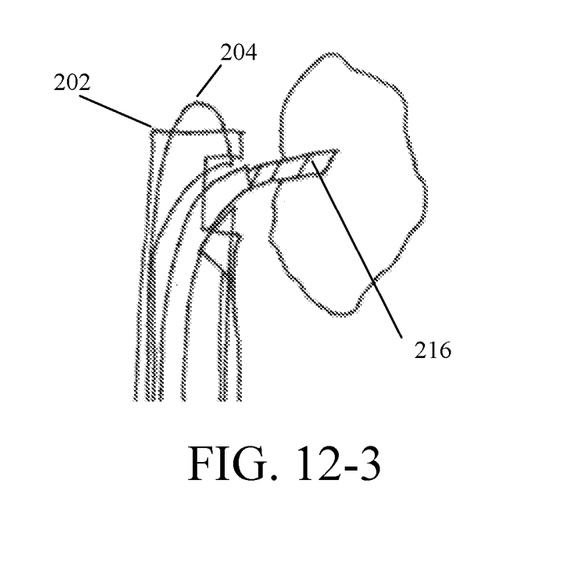

As shown in FIG. 12-2, a transducer 210, the exit ramp 206 would be positioned distally relative to the guide sheath window. After the tumor is located, the internal catheter would be pulled proximally so that the ramp of the inner catheter aligns with the window, allowing the needle to exit the guide sheath through the window.

A. A system comprising: a display device; a scope device comprising: a handle; an insertion tube having a proximal end attached to the handle and a working channel; and a camera located at a distal end of the insertion tube adjacent to the working channel, the camera is configured to generate images approximately along a longitudinal axis associated with the insertion tube; a guide sheath received within the working channel, the guide sheath comprising: a window occupying a predefined circumferential sector of a distal end of the guide sheath; and a plurality of markings configured to visually indicate location of the window, the plurality of markings comprising: a plurality of first markings located along a longitudinal center axis of the window; and a plurality of second markings located along one or more other longitudinal axes that are radially separated from the longitudinal center axis of the window by more than 45°; and a radial ultrasound device configured to be received within the guide sheath, the radial ultrasound device comprises a radial transducer positioned at the window and configured to send image signals to the display device.

B. The system of A, wherein the plurality of first markings comprises two or more pointer markers that point along the longitudinal center axis towards the window.

C. The system A or B, wherein the plurality of second markings comprises two or more pointer markings that point in the shortest direction towards the longitudinal center axis of the window along the circumference of the guide sheath.

D. The system of A, B or C, wherein the plurality of second markings comprises two or more non-pointer markers located on a side of the guide sheath that is approximately opposite to a side associated with the window.

E. The system of A, B, C or D, further comprising one or more additional windows located at both a circumferentially different position and a longitudinally different position than the window.

F. The system of A, B, C, D or E, wherein at least a portion of the plurality of first markers indicates a distance value associated with the window for a center of the window.

G. The system of A, B, C, D, E or F, wherein the portion of the markers indicates a distance between the window or the center of the window and a distal end of at least one of a sheath or the working channel.

H. The system of A, B, C, D, E, F or G, wherein portion of the markers comprises one or more first symbols and one or more second symbols, wherein the first symbols and second symbols are different.

I. The system of A, B, C, D, E, F, G or H, wherein the radial ultrasound device is a radial endobronchial ultrasound.

J. The system of A, B, C, D, E, F, G, H or I, wherein the scope device further comprises an ultrasound transducer.

K. The system of any of A-J, further comprising a sampling device having a distal end configured to exit the working channel at the window upon receiving a distal force.

L. The system of any of A-J, further comprising a medicant delivery device having a distal end configured to exit the working channel at the window upon receiving a distal force.

M. An apparatus comprising: a guide sheath received within the working channel, the guide sheath comprising: a window occupying a predefined circumferential sector of a distal end of the guide sheath; and a plurality of markings configured to visually indicate location of the window, the plurality of markings comprising: a plurality of first markings located along a longitudinal center axis of the window; and a plurality of second markings located along one or more other longitudinal axes that are radially separated from the longitudinal center axis of the window by more than 45°; and a radial ultrasound device configured to be received within the guide sheath, the radial ultrasound device comprises a radial transducer positioned at the window and configured to send image signals to the display device.

N. The apparatus of M, wherein the plurality of first markings comprises two or more pointer markers that point along the longitudinal center axis towards the window.

O. The apparatus of M or N, wherein the plurality of second markings comprises two or more pointer markings that point in the shortest direction towards the longitudinal center axis of the window along the circumference of the guide sheath.

P. The apparatus of any of M-O, wherein the plurality of second markings comprises two or more non-pointer markers located on a side of the guide sheath that is approximately opposite to a side associated with the window.

Q. The apparatus of any of M-P, further comprising one or more additional windows located at both a circumferentially different position and a longitudinally different position than the window.

R. The apparatus of any of M-Q, wherein at least a portion of the plurality of first markers indicates a distance value associated with the window for a center of the window.

S. The apparatus of any of M-R, wherein the portion of the markers indicates a distance between the window or the center of the window and a distal end of at least one of a sheath or a delivery device.

T. The apparatus of A any of M-S, wherein the portion of the markers comprises one or more first symbols and one or more second symbols, wherein the first symbols and second symbols are different.

U. The apparatus of any of M-T, wherein the radial ultrasound device is a radial endobronchial ultrasound.

The description of the invention is merely exemplary in nature and variations that do not depart from the gist of the invention are intended to be within the scope of the invention. Such variations are not to be regarded as a departure from the spirit and scope of the invention.

What is claimed is:

1. A system comprising:
  a display device;
  a scope device comprising:
    a handle;
    an insertion tube comprising:
      a proximal end attached to the handle;
      a working channel; and
      a camera located at a distal end of the insertion tube adjacent to the working channel, wherein the camera is configured to communicate image signals to the display device; and
  a guide sheath received within the working channel, the guide sheath comprising:
    at least one window occupying a predefined circumferential sector of a portion of a distal end of the guide sheath; and
    a plurality of markings configured to visually indicate location of the at least one window, the plurality of markings comprising:
      a plurality of first markings located along a longitudinal center axis of the at least one window; and
      a plurality of second markings located along one or more other longitudinal axes that are radially separated from the longitudinal center axis of the at least one window by more than 45°.

2. The system of claim 1, wherein the plurality of first markings comprises two or more pointer markers that point along the longitudinal center axis towards the at least one window.

3. The system claim 2, wherein the plurality of second markings comprises two or more pointer markings that point in the shortest direction towards the longitudinal center axis of the at least one window along the circumference of the guide sheath.

4. The system of claim 3, wherein the plurality of second markings comprises two or more non-pointer markers located on a side of the guide sheath that is approximately opposite to a side associated with the at least one window.

5. The system of claim 1, wherein at least a portion of the plurality of first markers indicates a distance value associated with the window for a center of the at least one window.

6. The system of claim 5, wherein the portion of the markers indicates a distance between the window or the center of the at least one window and a distal end of at least one of a sheath or the working channel.

7. The system of claim 5, wherein the portion of the markers comprises one or more first symbols and one or more second symbols, wherein the first symbols and second symbols are different.

8. The system of claim 1, further comprising a radial ultrasound device configured to be received within the guide sheath, wherein the radial ultrasound device comprises a radial transducer configured to send image signals to the display device when positioned at the at least one window.

9. The system of claim 1, further comprising a sampling device having a distal end configured to exit the working channel at the at least one window upon receiving a distal force.

10. The system of claim 1, further comprising a medicant delivery device having a distal end configured to exit the working channel at the at least one window upon receiving a distal force.

11. An apparatus comprising:
  a guide sheath configured to be received within a working channel of a bronchoscope, the guide sheath comprising:
    a window occupying a predefined circumferential sector of a distal end of the guide sheath; and a plurality of markings configured to visually indicate location of the window, the plurality of markings comprising:
  a plurality of first markings located along a longitudinal center axis of the window; and
  a plurality of second markings located along one or more other longitudinal axes that are radially separated from the longitudinal center axis of the window by more than 45°.

12. The apparatus of claim 11, wherein the plurality of first markings comprises two or more pointer markers that point along the longitudinal center axis towards the window.

13. The apparatus of claim 12, wherein the plurality of second markings comprises two or more pointer markings that point in the shortest direction towards the longitudinal center axis of the window along the circumference of the guide sheath.

14. The apparatus of claim 13, wherein the plurality of second markings comprises two or more non-pointer markers located on a side of the guide sheath that is approximately opposite to a side associated with the window.

15. The apparatus of claim 11, wherein at least a portion of the plurality of first markers indicates a distance value associated with the window for a center of the window.

16. The apparatus of claim 15, wherein the portion of the markers indicates a distance between the window or the center of the window and a distal end of at least one of a sheath or a delivery device.

17. The apparatus of claim 15, wherein the portion of the markers comprises one or more first symbols and one or more second symbols, wherein the first symbols and second symbols are different.

18. The apparatus of claim 11, wherein the guide sheath further comprises:
  a lumen connected between the window and a proximal end of the guide sheath; and
  a ramp located within the lumen adjacent the window, the ramp configured to direct tools received within the lumen towards the window.

19. The apparatus of claim 11, wherein the guide sheath further comprises a port at the distal end of the guide sheath,
  further comprising a catheter received within a lumen of the guide sheath, the catheter comprising:
    at least a portion configured of an ultrasound permeable material;
    a distal port; and
    a lumen comprising a ramp section connected to the distal port.

* * * * *